(12) United States Patent
Bampton et al.

(10) Patent No.: US 11,137,469 B2
(45) Date of Patent: Oct. 5, 2021

(54) METHOD AND DEVICE FOR CONTROLLING A MAGNETIC RESONANCE IMAGING SYSTEM

(71) Applicant: Siemens Healthcare GmbH, Erlangen (DE)

(72) Inventors: Adrian Bampton, Abingdon (GB); Stephan Biber, Erlangen (DE); Adam Paul Johnstone, Thame (GB); Jürgen Nistler, Erlangen (DE); Andreas Potthast, Erlangen (DE); Markus Vester, Nuremberg (DE); Andre de Oliveira, Uttenreuth (DE)

(73) Assignee: Siemens Healthcare GmbH, Erlangen (DE)

( * ) Notice: Subject to any disclaimer, the term of this patent is extended or adjusted under 35 U.S.C. 154(b) by 0 days.

(21) Appl. No.: 16/875,547

(22) Filed: May 15, 2020

(65) Prior Publication Data
US 2020/0363489 A1 Nov. 19, 2020

(30) Foreign Application Priority Data
May 15, 2019 (EP) .................................... 19174690

(51) Int. Cl.
*G01R 33/58* (2006.01)
*A61B 5/055* (2006.01)
(Continued)

(52) U.S. Cl.
CPC .............. *G01R 33/58* (2013.01); *A61B 5/055* (2013.01); *G01R 33/543* (2013.01); *G01R 33/5608* (2013.01)

(58) Field of Classification Search
USPC ........................................................ 324/318
See application file for complete search history.

(56) References Cited

U.S. PATENT DOCUMENTS

| 2014/0347049 A1 | 11/2014 | Tsai |
| 2019/0107591 A1 | 4/2019 | Aley |
| 2020/0064425 A1* | 2/2020 | Biber ..................... A61B 5/055 |

FOREIGN PATENT DOCUMENTS

| EP | 3467532 A1 | 4/2019 |
| EP | 3614163 A1 | 2/2020 |

OTHER PUBLICATIONS

Aley, Nicholas et. al., "Automatic Ramping of Magnet Resonance Systems Using Fixed Installed Nuclear Magnetic Resonance Probes for Magnet Current Sensing", 2016. pp. 1-3.
(Continued)

*Primary Examiner* — Rodney E Fuller
(74) *Attorney, Agent, or Firm* — Lempia Summerfield Katz LLC (57) ABSTRACT

A calibration method for calibrating a measuring element for determining an electric current flowing through a basic-field magnet of a magnetic resonance imaging system includes performing a measurement with the measuring element, and performing a frequency measurement in the magnetic field of the basic-field magnet with a frequency measuring unit. The measurement of the measuring element and the frequency measurement are corresponding to the same magnetic field of the basic-field magnet. The calibration method also includes calculating a calibration factor based on a deviation between the measurement with the measuring element and the frequency measurement, and calibrating the measuring element or the electric current in the basic-field magnet based on the calibration factor.

20 Claims, 4 Drawing Sheets

(51) Int. Cl.
G01R 33/54 (2006.01)
G01R 33/56 (2006.01)

(56) References Cited

OTHER PUBLICATIONS

European Search Report for European Application No. 19174690.8-1022 dated Dec. 12, 2019.

* cited by examiner

METHOD AND DEVICE FOR CONTROLLING A MAGNETIC RESONANCE IMAGING SYSTEM

This application claims the benefit of European Patent Application No. EP 19174690.8, filed on May 15, 2019, which is hereby incorporated by reference in its entirety.

BACKGROUND

The present embodiments relate to a calibration method and a system for calibrating a measuring element for determining an electric current flowing through a basic-field magnet of a magnetic resonance imaging system.

In the technical field of magnetic resonance imaging (MRI) systems, relatively high fields are to be applied by typically using electromagnets for creating the basic field. Since for high magnetic fields, high electric currents in the order of about 500 A are to be applied, superconducting magnets with a persistent switch may be used as basic field magnets.

These superconducting magnets are "filled" with a current in a ramping procedure by using a magnet power supply unit (MPSU). When the optimal magnetic field is reached, the persistent switch, which is also superconducting, is closed, and the current will flow for a long time period in the superconducting magnet forming the basic field of the MRI-system.

Unfortunately, there is a little loss of current over the time, resulting in a slowly decreasing magnetic field. In any superconducting MRI system, decay of the magnetic field is unavoidable due to the residual electrical resistance of the magnet. The field decay results in a drift of the target frequency measured in the main magnetic field. The decay of the magnetic field lies typically in the order of several hundred ppm per year.

Although a body coil of an MRI-system is typically configured such that the target frequency generally exceeds the center frequency of the body coil by an amount that is sufficient to ensure that the center frequency of the main magnetic field remains above the body coil center frequency for as long as possible, the basic field magnet is to be re-ramped from time to time. The fact that the drift of the target frequency results not only in an ineffective measurement, but also in reflections of the RF-Signals used for measurement is to be taken into account. Higher reflection coefficients for frequencies off the center frequency significantly reduce the available power from the radio frequency power amplifier (RFPA) of the MRI-system. If the reflection coefficients from the body coil are not equal, the reflected power is not sent through the hybrid to the 50 ohm dummy load but partly reflected back into the RFPA, which leads to a derating of the RFPA. This is an additional effect, which reduces the available power for B1 field generation.

In a high-field MRI-system with a basic magnetic field greater than 1 T, the bandwidth of the body coil and radio-frequency system is so large (e.g., body coil bandwidth ±100 kHz or more) that it may take several years before field decay is out of specification. However, in low field MRI-systems with a basic magnetic field of 1 T or below, which may be preferred on account of their smaller footprint, field decay affects measurements much more. Typically, the bandwidth of a low-field system is significantly narrower than that of a high-field system, being only in the order of 10 kHz-25 kHz, so that prior art methods of setting the magnet target frequency are limited to a much shorter "decay window". Because the decay window is narrower, the magnet frequency of a low-field MRI system decays towards an out-of-spec level in a shorter space of time. This provides that low-field MRI systems are to generally be ramped more often.

When an MRI-system is first installed on site, a ramping procedure is carried out to set up the basic magnetic field (e.g., the static background field) in the main coil windings (e.g., basic field magnet). After the initial installation ramping procedure, shim coils are used to perform any adjustments necessary to take into account the local environment. Usually, the target frequency (e.g., the center frequency for measurements in the basic field) is determined with the aid of a frequency measuring unit placed at a suitable position in the apparatus.

Before ramping the magnet, a target frequency for the main magnetic field is identified. The highest possible target frequency may be set, and the shim coils may be used for any fine-tuning of the main magnetic field. By setting the highest possible target frequency, the decay window (e.g., the time taken for the frequency to drift out of specification, such as to the lower end of the allowed band) is made as long as possible. This approach is suitable for systems with a high bandwidth, as explained above.

After a certain time on the order of about one year for low field MRI-systems or of several years of high field MRI-systems, a ramping procedure is to be applied to install an optimal basic magnetic field again. In the course of the ramping procedure, the basic field magnet is usually ramped down (e.g., to a magnetic field of zero or at least to a lower field strength) and then up again to the field where the optimal target frequency for measurement is reached. The term "ramping procedure" is thus used to refer to the whole procedure to reach a desired magnetic field from an actual magnetic field; usually at first the magnet is ramped down from the actual magnetic field and then is ramped up again to the desired magnetic field (e.g., possibly after a waiting time). However, the term "ramping procedure" may also refer to a single ramping-up or a single ramping-down (e.g., a ramping-up from an actual field of zero). In the following examples, it is often assumed that at the beginning of a ramping process, there is a ramping-down, and at the end of a ramping process, there is a ramping-up of the basic-field magnet.

Regarding the accuracy of the basic magnetic field, the electric current for driving the basic field magnet during ramping up is measured with a measuring device that is typically a voltmeter measuring the voltage over a shunt resistance.

The accuracy of the MPSU and corresponding sensors is a key problem that is to be solved to allow successful ramping procedure (e.g., an auto-ramp up) or to apply field-bumps to compensate for the field decay over time.

This accuracy is limited by the accuracy of the shunt resistance of known MPSU. Due to aging effects that are until now not fully known for MRI-systems, the shunt resistance slowly changes so that the measured voltage does not give a correct image of the exact current any more after some years. This effect does not only occur in superconducting MRI-systems but also in non-superconducting MRI-systems, as well.

Regarding superconducting magnets, another issue is to be taken into account: superconducting MRI-systems with low Helium content are more dependent on power and cooling infrastructure and corresponding reliability than systems with big Helium buffers. One mitigation to reduce the potential downtime of such systems is to deploy a magnet power supply unit (MPSU) as a part of the system, which is able to automatically ramp the system down in case, for example, of a power outage and to ramp the system back up. The MPSU may also be used to overcome problems with the field decay over time and the very narrow bandwidth of the RF system.

SUMMARY AND DESCRIPTION

The scope of the present invention is defined solely by the appended claims and is not affected to any degree by the statements within this summary.

The present embodiments may obviate one or more of the drawbacks or limitations in the related art. For example, in improved ramping of a magnetic resonance imaging system is provided.

A method according to an embodiment for calibrating a measuring element for determining an electric current flowing through a basic-field magnet of a magnetic resonance imaging system includes the following acts.

A measurement is performed with the measuring element. In this act, typically, a measurement, from which an electric current I flowing through a basic-field magnet of an magnetic resonance imaging system may be determined, is performed. Since for most applications it is not possible to measure the electric current directly (e.g., in a superconducting magnet with a persistent switch) or it is not advantageous, often, another parameter that is strongly connected with the electric current is measured. An example is the above described way to measure a voltage over a shunt resistance. In this case, a voltage measuring device (e.g., a voltmeter) and a shunt resistance may be part of the measuring element.

A frequency measurement is performed. In this act, a frequency is measured in the magnetic field of the basic-field magnet with a frequency measuring unit. Such frequency measurement (e.g., the measurement of the Larmor frequency of a proton in the magnetic field) is well known in the art. It is clear that the frequency measuring unit is not the measuring element so that the frequency measurement is independent from the measurement of the measuring element. It is important that the measurement of the measuring element and the frequency measurement are corresponding to the same magnetic field of the basic-field magnet. This provides that there is no ramping procedure between these two measurements. However, since the decay of the magnetic field is very slow, there may be days, weeks, or even month(s) between the two measurements as long as the magnetic field has not seriously changed. The time between the two measurements scales with a systematic error that may be minimized by minimizing the time gap between the two measurements.

For example, the measurement of the measuring element is performed at the beginning of the ramping procedure (e.g., at the beginning of the ramp-down), and the frequency measurement is performed before the ramping procedure (e.g., during the last examination of a patient). Alternatively, the measurement of the measuring element is performed at the end of the ramping procedure (e.g., at the end of ramp-up), and the frequency measurement is performed after the ramping procedure (e.g., with a phantom or during the following examination of a patient). In the case when a non-superconducting basic-field magnet is used, the measurements may be performed any time.

A calibration coefficient is calculated. The calibration coefficient is calculated based on the deviation between the measurement of the measuring element and the frequency measurement. How this deviation is taken into account depends on the used mathematical procedure and the used measuring components. For example, the frequency measurement offers direct information about the magnetic field, giving the opportunity to calculate the electric current that is flowing in the magnet. Regarding a measuring element with a shunt and a voltmeter, as mentioned above, the measuring element uses a given resistance of the shunt and a measured voltage for determining the electric current for ramping or driving the basic-field magnet. By using the voltage measured by the measuring element and the deviation of the two determined currents (e.g., from the voltage measurement and from the frequency measurement) the deviation of the resistance of the shunt may be directly calculated by using Ohm's law. Although the calibration coefficient may be a multiplier, the calibration coefficient may also be a summand or another suitable mathematical value.

The system is calibrated. A calibration of the measuring element or the electric current in the basic-field magnet is done based on the calibration coefficient. This provides that the measuring element is calibrated to reflect the correct electric current again with a next measurement. The electric current flowing in the basic-field magnet may, however, also be calibrated by correcting this electric current to install a correct magnetic field. This may be achieved, for example, with another "micro ramping", where a current is added to the magnet or drawn from the magnet.

The results of the calibration method may be directly used for optimizing the ramping procedure of a basic field magnet of an MRI-system, since the current for ramping up to the desired field is measured more accurately with a well calibrated measuring element.

A ramping method according to the present embodiments for controlling the ramping (e.g., the ramping-up or the complete ramping procedure) of a basic-field magnet of a magnetic resonance imaging system includes the following act.

A basic-field magnet of a magnetic resonance imaging system is ramped. The magnetic field of the basic-field magnet is ramped from a first magnetic field-strength to a second magnetic field-strength. The electric current flowing in the basic-field magnet is determined by a measuring element. The measuring element is calibrated with a method according to the present embodiments.

A system according to the present embodiments for calibrating a measuring element for determining the electric current I flowing through a basic-field magnet of a magnetic resonance imaging system includes the following components.

A first data interface is configured to read data from the measurement of the measuring element. The measuring element may be part of the system or may be an external unit sending the measured values to the system.

A second data interface is configured to read data from a frequency measuring unit configured for performing a frequency measurement. This second data interface may be identical with the first data interface. The frequency measuring unit may also be part of the system or may also be an external unit sending the measured values to the system. Suitable frequency measuring units are well known in the art.

For the present embodiment, the system is configured such that the data of the measurement of the measuring element and the data of the frequency measurement are selected to correspond to the same magnetic field of the basic-field magnet. In one embodiment, the system is configured to control the time of measurement or to select data from a dataset of measurements accordingly.

A calculation unit is (e.g., a processor) configured for calculating a calibration coefficient based on the deviation between the measurement of the measuring element and the frequency measurement.

A calibration unit (e.g., the processor or another processor) is configured for calibrating the measuring element based on the calibration coefficient. A calculation of the calibration coefficient may be performed as explained above.

The system may also include a current determination unit configured for determining the electric current flowing through a basic-field magnet of an magnetic resonance imaging system based on a measurement of the measuring element. The current determination unit may be a computing unit with the measuring element or at least with a data interface to read the measured values of the measuring element. The above-mentioned calculation unit may include the computing unit configured to determine the electric current.

A magnet power supply unit according to the present embodiments for driving a basic-field magnet of a magnetic resonance imaging system includes an embodiment of a system and/or is configured to perform a calibration method according to the present embodiments and/or a ramping method according to the present embodiments. The magnet power supply unit (MPSU) may include additional units or devices for controlling the process of driving and/or ramping a basic field magnet (e.g., a transformer, an amplifier, a controller, or protection diodes).

A control device according to the present embodiments for controlling a magnetic resonance imaging system includes a system according to the present embodiments and/or is configured to perform a calibration method according to the present embodiments and/or a ramping method according to the present embodiments. The control device may include additional units or devices for controlling components of a magnetic resonance imaging system (e.g., a sequence control unit for measurement sequence control, a memory, a radio-frequency transmission device that generates, amplifies, and transmits RF pulses, a gradient system interface, a radio-frequency reception device to acquire magnetic resonance signals and/or a reconstruction unit to reconstruct magnetic resonance image data).

A magnetic resonance imaging system according to the present embodiments includes a control device according to the present embodiments and/or a magnet power supply unit according to the present embodiments.

Some units or modules of the system, the MPSU, or the control device mentioned above may be completely or partially realized as software modules running on a processor of a system, the MPSU, or a control device. A realization largely in the form of software modules may have the advantage that applications already installed on an existing system may be updated, with relatively little effort, to install and run these units of the present application. In one embodiment, a computer program product with a computer program that is directly loadable into the memory of a device of a system, an MPSU, or a control device of a magnetic resonance imaging system is provided. The computer program product includes program units to perform the act of the method when the program is executed by the control device, the MPSU, or the system. In addition to the computer program, such a computer program product may also include further parts such as documentation and/or additional components, also hardware components such as a hardware key (e.g., dongle, etc.) to facilitate access to the software.

A computer readable medium (e.g., a non-transitory computer-readable storage medium) such as a memory stick, a hard-disk, or other transportable or permanently-installed carrier may serve to transport and/or to store the executable parts of the computer program product so that these may be read from a processor unit of a control device, an MPSU, or a system. A processor unit may include one or more microprocessors or equivalents.

Features of different categories (e.g., methods and systems) may be combined as appropriate to give further embodiments not described herein.

According to one embodiment of a calibration method, the calibration of the measuring element is performed by calculating corresponding parameters from the measurement of the measuring element and the frequency measurement. "Corresponding" provides that these parameters have the same physical dimension. This has the advantage that the parameters are easily comparable. The corresponding parameters may be a magnetic field, an electric current, or a frequency. For example, an electric current is determined from each of the measurements, and then, the two values for the electric current are compared.

The calibration coefficient may be determined as an aging factor of the measuring element based on the difference of these corresponding parameters. For the example of the above mentioned shunt resistance, the aging factor may reflect the drift of the resistance over time. In the above example where the measuring element includes a shunt and a voltmeter, the resistance R of the shunt is known but slowly changes over time. When the voltage V over the shunt is measured, the electric current I in the magnet is provided by $I=U/R$. The basic magnetic field B scales linearly with the electric current in the basic-field magnet and with the frequency that may be measured by the frequency measurement. Thus, with a constant factor $1/a$, considering this linearity, the resistance of the shunt may be calculated by $R=a \cdot U/f$. This is the real resistance of the shunt in the borders of measuring errors. However, the measurements may be accomplished with a high accuracy in a region far more exact than the normal tolerance of the shunt. Thus, the 'real' initial resistance R, of the shunt may be determined first, and after years, the aging of the shunt may be determined by comparing the initial resistance $R_i$ (e.g., determined or predefined) with the actual determined resistance With a calibration factor $C=(a \cdot U)/(f \cdot R_i)$, the shunt may be calibrated by the multiplication $R_i \cdot C$. In addition, after some determinations of C over time, an aging curve of the shunt over time may be determined.

Generally, for the frequency measurement, the Larmor frequency of protons may be measured in a phantom (e.g., a typical test object in MRI) or during a patient scan. This procedure is commonly known.

According to one embodiment of a calibration method, a measurement of the measuring element is performed at the beginning of a ramping procedure. The frequency measurement may then be performed before the ramping procedure, since the magnetic field for the measurements is to be the same.

In one embodiment, where the base-field magnet is a superconducting magnet with a persistent switch, it is not possible to "look" inside the magnet and measure the electric current directly, since the condition of superconductivity does not allow measurements (e.g., voltage measurements, since there is no resistance). In this case, the electric current may be measured at the moment of ramping down the basic-field magnet at the beginning of the ramping procedure. The ramping down is performed by opening the persistent switch (e.g., by heating the persistent switch) to a condition out of superconductivity. With the switch as resistance, the electric current will flow through the MPSU and typically transformed to heat in resistors or protection diodes.

Thus, after the opening (e.g., heating) of the persistent switch, a part of the electric current of the basic-filed magnet flows through the measuring element. However, at the very beginning, in the order of several milliseconds, there is no linear or even regular flow of electric current, but a chaotic phase followed by a transient phase.

In one embodiment, the electric current that was flowing in the basic-field magnet before or at the point of time of opening the persistent switch is determined in this case by determining a time resolved current-curve based on the measurement of the measuring element. Thus, the measuring element is used to record a vast number of measurements (e.g., taken every some milliseconds). For example, this time resolved current-curve may be reconstructed to the point of time of opening the persistent switch. This may be achieved with a model of a current curve. For example, since the shape of the current curve may be simulated, it is also possible to reconstruct the very beginning of this current curve in the simulation. The simulated current curve may be scaled (e.g., by adjusting coefficients of this curve) in order to be adjusted to the measured current-curve. Then, the start of the simulated current-curve (e.g., at the point of time opening the switch) provides the value of the electric current in the magnet at the point of time of opening the switch (e.g., also the electric current flowing in the magnet before opening the switch). The electric current may also be determined by a machine learning algorithm trained to reconstruct the current-curve in an adequate manner or by measurements where the electric current in the magnet is determined with another measuring unit (e.g., the frequency measuring unit) at a point in time where no aging has occurred to the measuring element. The determined electric current may be brought in connection with the shape of the current-curve and after a series of measurements is possible to determine the electric current by the shape of the current-curve by using a lookup table or a formula.

According to an embodiment of a calibration method, a measurement of the measuring element is performed at the end of a ramping procedure (e.g., the end of the ramping up; just before the persistent switch is closed in a superconducting magnet). The frequency measurement may then be performed after the ramping procedure, since the magnetic field for the measurements is to be the same. Regarding the above mentioned measurement at the beginning of the ramping procedure, both measurements may be performed, one at the beginning and one at the end of the ramping procedure.

According to an embodiment of a calibration method, a frequency measurement is performed during a patient scan (e.g., the next patient scan after the ramping procedure). This has the advantage that it is not necessary to install a phantom or another test object in the MRI-system and measure the frequency there. The frequency measurement may be easily recorded automatically during the next patient scan. Then, the calibration of the measuring element may easily be done based on this frequency measurement. The ramping procedure will, for example, be ended in a state where the actual aging of the measuring element measured in the preceding ramping procedure is taken into account. Thus, in low-field MRI-systems, the calibration of the measuring element will be about one year behind. This is not, however, dramatic, since the aging is a very slow process, and the accuracy of the calibration method will nevertheless be sufficient for the performance of the MRI-system.

To enhance the accuracy of the calibration, the actual calibration may be adjusted based on a chronological sequence of succeeding calibration coefficients measured at different time points or a predefined aging curve. Until now, the aging curve of, for example, a shunt resistance in an MRI-system is not yet known exactly. It is, however, possible to easily measure the aging curve in the course of the calibration method by recording the calibration coefficients over the time (e.g., over the ramping procedures). Depending on the theory of the aging process, after some measurements, an aging curve may be determined (e.g., a linear or polynomial progression), and the calibration may be further adjusted. Later, when enough data is recorded, an aging curve may be determined and provided for the calibration method. Although it is always possible to use this very curve for calibration, the calibration method according to the present embodiments is nevertheless advantageous, since the correctness of the aging curve may be examined, and chaotic effects may be excluded (e.g., a fixed aging curve may be adjusted to reality).

According to an embodiment of a calibration method, the electric current I flowing through the basic-field magnet is determined by measuring the voltage V over a shunt resistance with a predefined or earlier calibrated value R and calculating I with the formula $I=U/R$. Examples for this embodiment have already been described above. In one embodiment, the calibration coefficient scales linear with the deviation of the measured frequency to a predefined target frequency $\Delta f$, or the calibration coefficient C is calculated based on the measured frequency f, a constant coefficient x, and the determined electric current I from $C = x \cdot I/f$, as similarly explained above concerning the measured voltage.

According to an embodiment of a ramping method, the measuring element is calibrated before a ramping procedure with the calibration coefficient calculated in the preceding ramping procedure. This has already been described above in the course of measurements at the end of the ramping procedure.

In one embodiment, the calibration coefficient is adjusted based on a condition coefficient from a predefined aging curve or calculated from an extrapolation of a chronological sequence of succeeding calibration coefficients measured at different time points. Regarding superconducting magnets, these time points are different ramping procedures.

According to an embodiment of a ramping method, after the calibration of the measuring element, but before the next ramping procedure, a ramp-adjusting procedure is performed. The electric current in the basic field magnet is installed based on the adjusted calibration of the MPSU measuring element. Thus, measurements for calibration may be made at the end of a ramping procedure, the measuring element may be calibrated, and then, after the original ramping, another "micro ramping" may be applied to adjust the current error in the magnet to the correct field current that is measured with the re-calibrated measuring element. This may, for example, be achieved in praxis with a frequency measurement at a phantom right after the ramping procedure, and then, the magnet may be re-ramped accordingly.

An advantage of the present embodiments is that the calibration of the measuring element may be automized, since all measurements, determinations/calculations may be performed in an automated manner. Thus, an auto-ramp up may be performed with the ramping method according to the present embodiments, as well as an auto ramp down. Thus, the present embodiments provide a solution for overcoming the problem of the aging effects taking the actual layout of the measuring element versus the diode pack and the superconductive switch into account and how to derive the calibration coefficients.

BRIEF DESCRIPTION OF THE DRAWINGS

Other objects and features of the present invention will become apparent from the following detailed descriptions considered in conjunction with the accompanying drawings. The drawings, however, are provided for the purpose of illustration and not as a definition of the limits of the invention.

DETAILED DESCRIPTION

In the diagrams, like numbers refer to like objects throughout. Objects in the diagrams are not necessarily drawn to scale.

Figure 1:
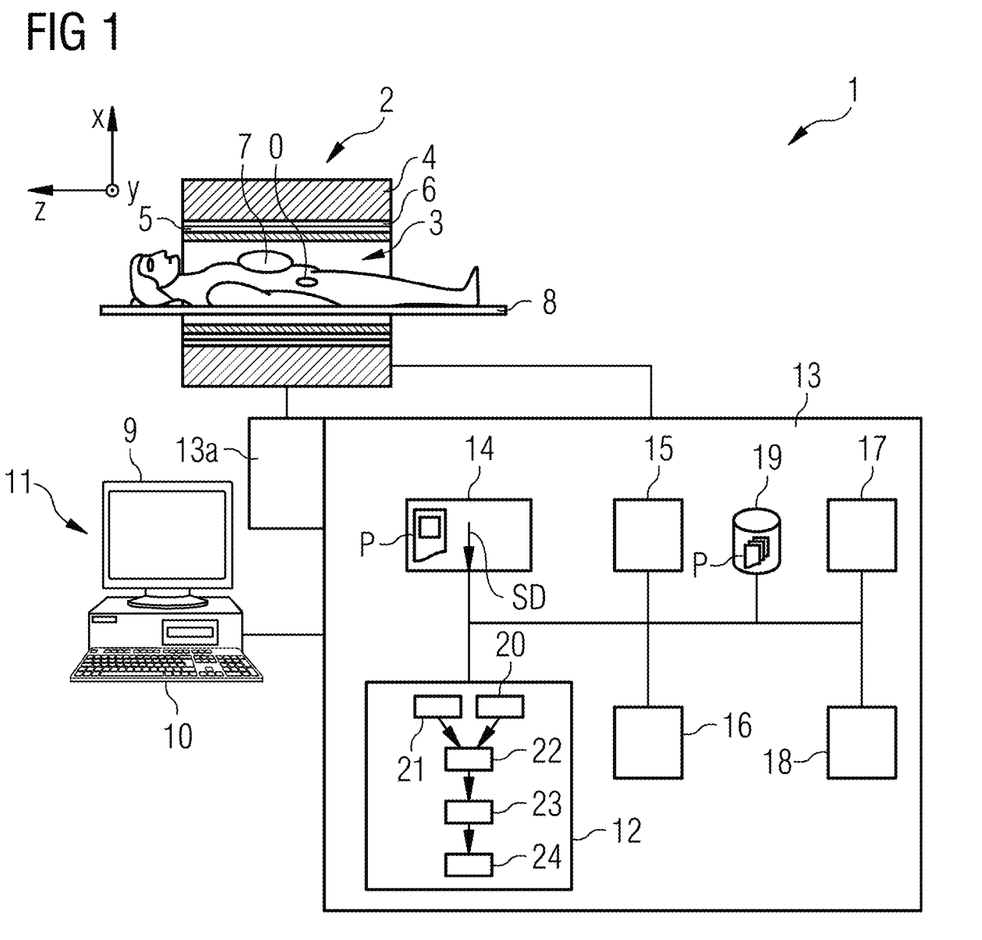
FIG. 1 shows a simplified magnetic resonance imaging (MRI) system with an example for a system according to an embodiment.

FIG. 1 shows a schematic representation of a magnetic resonance imaging (MRI) system 1. The MRI system 1 includes an actual magnetic resonance scanner 2 (e.g., a data acquisition unit) with an examination space 3 or patient tunnel in which a patient or test person is positioned on a driven bed 8. An examination object is located within the patient or test person.

The magnetic resonance scanner 2 is typically equipped with a basic field magnet system 4, a gradient system 6, and a radio-frequency (RF) transmission antenna system 5 and an RF reception antenna system 7. In the shown exemplary embodiment, the RF transmission antenna system 5 is a whole-body coil permanently installed in the magnetic resonance scanner 2, in contrast to which the RF reception antenna system 7 is formed as local coils (symbolized here by only a single local coil) to be arranged on the patient or test subject. In principle, however, the whole-body coil may also be used as an RF reception antenna system, and the local coils may respectively be switched into different operating modes.

The basic field magnet system 4 is configured such that a region of Interest ("RoI") may be recorded. The basic field magnet system 4 is configured to generate a basic magnetic field in a longitudinal direction of the patient (e.g., along the longitudinal axis of the magnetic resonance scanner 2 that proceeds in the z-direction). The gradient system 6 typically includes individually controllable gradient coils in order to be able to switch (e.g., activate) gradients in the x-direction, y-direction, or z-direction independently of one another.

The MRI system 1 shown in FIG. 1 is a whole-body system with a patient tunnel into which a patient may be completely introduced. However, the present embodiments may also be used at other MRI systems (e.g., with a laterally open, C-shaped housing), as well as in smaller magnetic resonance scanners in which only one body part may be positioned.

The MRI system 1 also has a central control device 13 that is used to control the MRI system 1. This central control device 13 includes a sequence control unit 14 for measurement sequence control. With this sequence control unit 14, the series of RF pulses and gradient pulses may be controlled depending on a selected pulse sequence or, respectively, a series of multiple pulse sequences to acquire magnetic resonance images of the RoI within a measurement session. For example, such a series of pulse sequence may be predetermined within a measurement or control protocol P. Different control protocols P for different measurements or measurement sessions may be stored in a memory 19 and may be selected by an operator (and possibly modified as necessary), and then be used to implement the measurement.

To output the individual RF pulses of a pulse sequence, the central control device 13 has a radio-frequency transmission device 15 that generates and amplifies the RF pulses and feeds the RF pulses into the RF transmission antenna system 5 via a suitable interface (not shown in detail). To control the gradient coils of the gradient system 6, the control device 13 has a gradient system interface 16. The sequence control unit 14 communicates in a suitable manner with the radio-frequency transmission device 15 and the gradient system interface 16 to emit the pulse sequence.

The control device 13 has a radio-frequency reception device 17 (likewise communicating with the sequence control unit 14 in a suitable manner) in order to acquire magnetic resonance signals (e.g., raw data) for the individual measurements. The magnetic resonance signals are received in a coordinated manner from the RF reception antenna system 7 within the scope of the pulse sequence.

A reconstruction unit 18 receives the acquired raw data and reconstructs magnetic resonance image data therefrom for the measurements. This reconstruction is typically performed based on parameters that may be specified in the respective measurement or control protocol. For example, the image data may then be stored in a memory 19.

Operation of the central control device 13 may take place via a terminal 10 with an input unit and a display unit 9, via which the entire MRI system 1 may thus also be operated by an operator. MR images may also be displayed at the display unit 9, and measurements may be planned and started by the input unit (possibly in combination with the display unit 9). Suitable control protocols may, for example, also be selected (and possibly modified) with suitable series of pulse sequence, as explained above.

The control device 13 includes a system 12 configured to perform the calibration method according to the present embodiments. This system 12 includes the following components that may partly appear to be software modules.

In this example, the system 12 includes a measuring element 20 and a frequency measuring unit 21. The measured data of both measuring components are provided via a data interface 22 (e.g., used for all measured data) to a calculation unit 23.

This calculation unit 23 is configured for calculating a calibration factor C based on the deviation between the measurement of the measuring element 20 and the frequency measurement.

The system also includes a calibration unit 24 that is configured for calibrating the measuring element 20 based on the calibration factor C. The calibrated measuring element may be used to measure the current delivered from a magnet power supply unit 13a that is, for example, strongly connected with the control unit 13. The calibrated measuring element may also be a complete external unit communicating with the control unit 13, or the system 12 may also be part of the MPSU 13a.

The MRI system 1 according to the present embodiments and, for example, the control device 13 and the MPSU 13a may have a number of additional components that are not shown in detail but are typically present in such systems (e.g., a network interface in order to connect the entire system with a network and be able to exchange raw data and/or image data or, respectively, parameter maps, but also additional data, such as patient-relevant data or control protocols). A more detailed example on an MPSU 13a is described below.

The manner by which suitable raw data is acquired by radiation of RF pulses and the generation of gradient fields, and MR images are reconstructed from the raw data, is known to those skilled in the art and thus need not be explained in detail herein.

Figure 2:
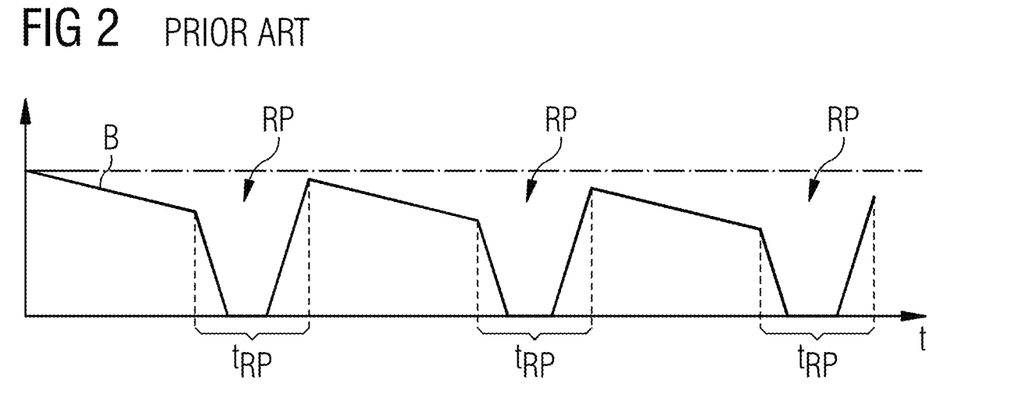
FIG. 2 shows an exemplary curve of a magnetic field in an MRI system of the state of the art.

FIG. 2 shows an exemplary curve of the magnetic field B in an MRI-system of the state of the art. On a horizontal time-axis t, the strength of the magnetic field B of the basic-field magnet 4 of the MRI-system 1 is shown over time. Starting from a predefined value, the strength of the magnetic field B of the basic-field magnet 4 slowly decays. After a while (e.g., one year), a ramping procedure RP is performed in the ramping time $t_{RP}$ to adjust the strength of the magnetic field B again. The ramping time $t_{RP}$ and the time for decay are not true to scale. As provided above, the time for decay is in the order of years, where the ramping time $t_{RP}$ lies in the order of days or hours.

Regarding the horizontal dash-dotted line, representing the desired strength (e.g., constant strength) of the magnetic field B, the desired strength is not reached again after the first ramping procedure RP, and the gap between the desired and reached magnetic field B steadily grows over the three ramping procedures RP that are shown. The reason for that gap is the aging of the measuring element 20 (see, e.g., FIG. 1). The system "thinks" that the desired magnetic field B has been reached due to the measurement of the measuring element at the end of the ramping procedure RP.

Figure 3:
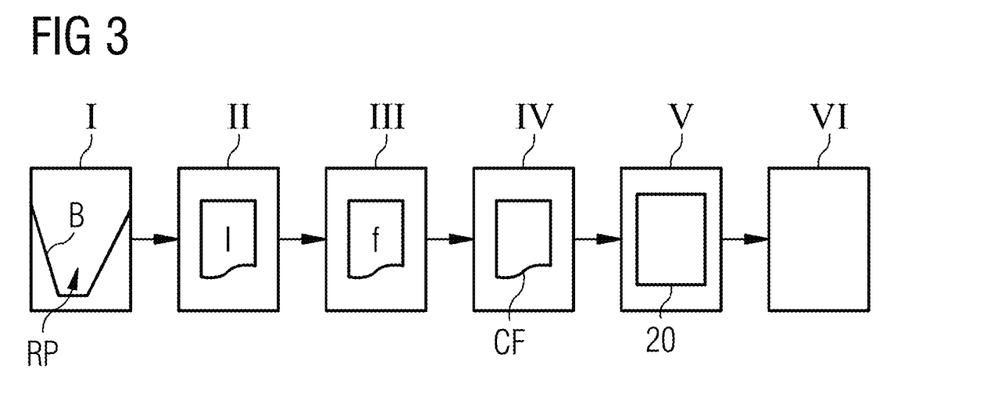
FIG. 3 shows a block diagram of a process flow of a ramping method and a calibration method according to an embodiment.

FIG. 3 shows a block diagram of the process flow of a preferred ramping method according to the present embodiments for controlling the ramping procedure RP of a basic-field magnet 4 of a magnetic resonance imaging system 1, (see, e.g. FIG. 1). This ramping method includes a calibration method according to the present embodiments for calibrating a measuring element 20 for determining the electric current I flowing through a basic-field magnet 4 of a magnetic resonance imaging system 1.

In act I, a ramping procedure RP is initiated.

In act II, a measurement is performed with the measuring element 20 from which the electric current I flowing through the basic-field magnet 4 may be determined. This measurement may be performed at the beginning of the ramping procedure RP; in this example, the measurement is performed at the end of the ramping procedure RP.

In act III, a frequency measurement is performed in the magnetic field B of the basic-field magnet 4. Since the measurement of the measuring element and the frequency measurement are corresponding to the same magnetic field of the basic-field magnet, this frequency measurement is performed after the ramping procedure in this example.

In act IV, a calibration factor CF is calculated based on the deviation between the measurement of the measuring element 20 and the frequency measurement.

In act V, the measuring element 20 is calibrated based on the calibration factor CF.

In act VI, also the electric current in the basic-field magnet 4 is calibrated based on the calibration factor with a small correction-ramping.

Figure 4:
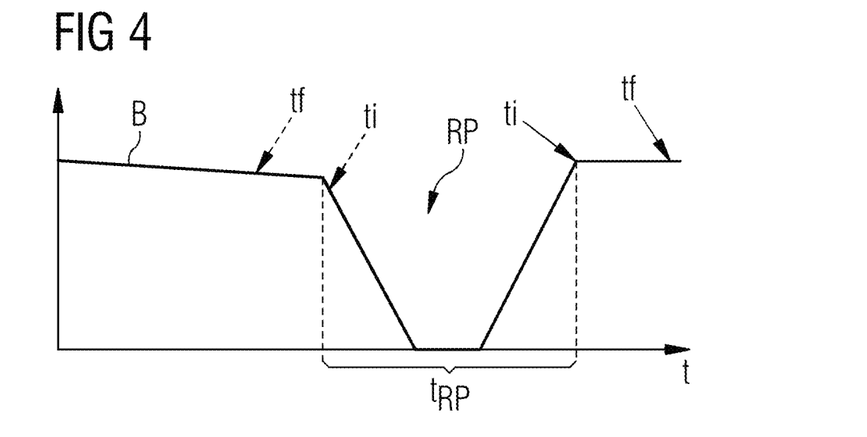
FIG. 4 shows an exemplary curve of the magnetic field during a ramping procedure.

FIG. 4 shows an exemplary curve of the magnetic field B during a ramping procedure RP. Shown are possible points of time for the measurements. The solid arrows show the time of a measurement with the measuring element ti and a time of the frequency measurement tr according to the example described in FIG. 3. However, alternative possible time points for these measurements are shown with the dashed arrows.

Figure 5:
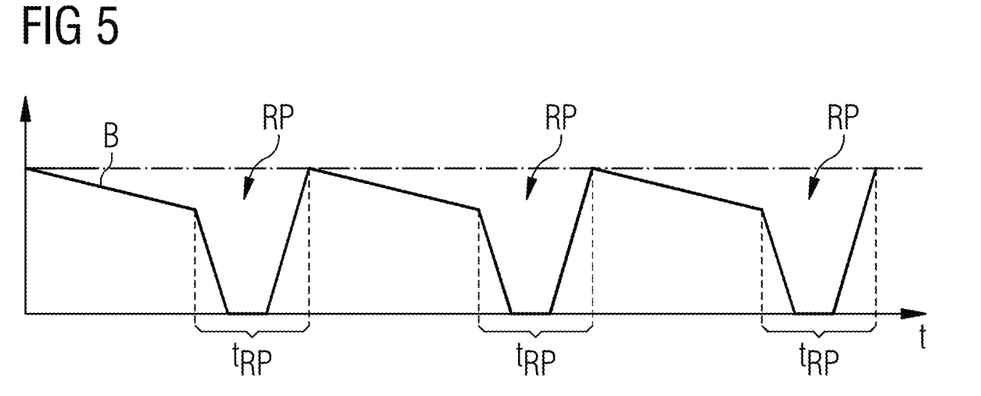
FIG. 5 shows an exemplary curve of the magnetic field in an MRI system according to an embodiment.

FIG. 5 shows an exemplary curve of the magnetic field B in a MRI-system 1 according to the present embodiments. FIG. 5 is similar to FIG. 2 with the important difference that always the desired magnetic field B is reached after any ramping procedure RP due to the calibration of the measuring element 20 (see FIG. 1).

Figure 6:
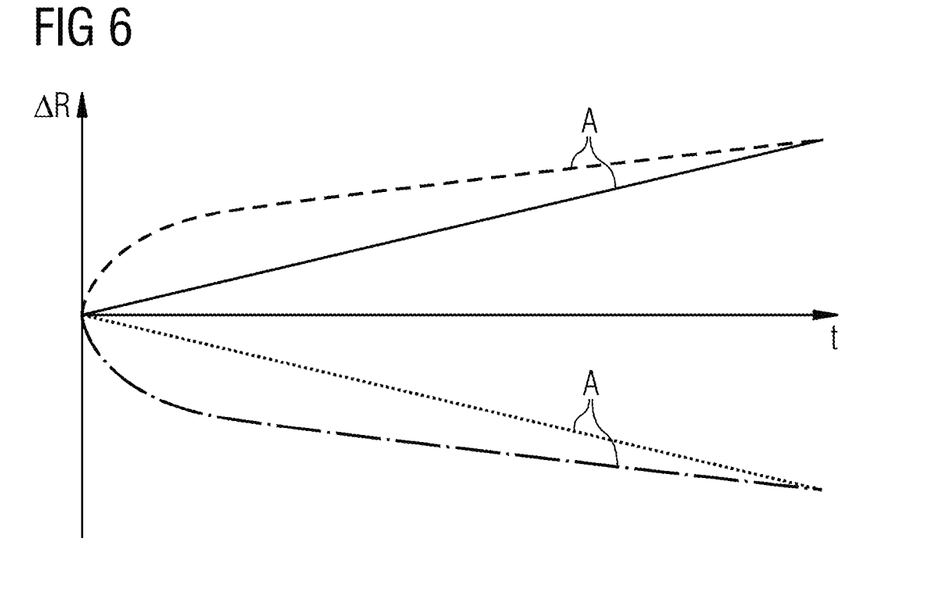
FIG. 6 shows examples of possible aging curves.

FIG. 6 shows examples of possible aging curves A. These aging curves A represent a deviation of the resistance ΔR of a shunt magnet 20b (see FIG. 7) over time t. Since the shape of an aging curve A is not yet known exactly in the field of MRI, there are some examples of possible aging curves A shown: one rising linearly and one rising in a polynomial way (e.g., a rising deviation of the of the resistance ΔR provides that the current I measured is higher than the real current), as well as one falling linearly and one falling in a polynomial way (e.g., a falling deviation of the of the resistance ΔR means that the current I measured is lower than the real current).

Figure 7:
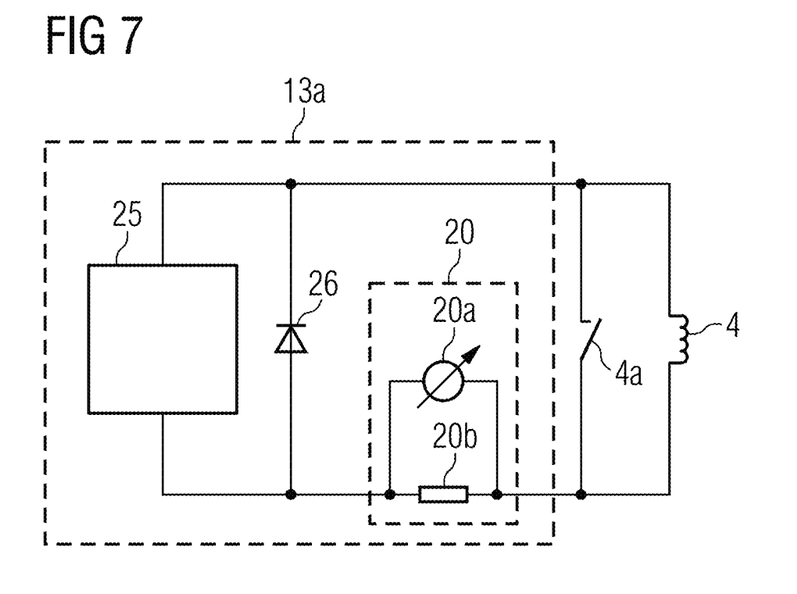
FIG. 7 shows an exemplary circuit of a superconducting magnet and a magnet power supply unit (MPSU) according to an embodiment.

FIG. 7 shows an exemplary circuit of a superconducting magnet and a magnet power supply unit (MPSU) according to an embodiment. Well known components that are not relevant for the present embodiments (e.g., transformers, amplifiers, etc.) are combined in a box "power supply" 25. The power supply delivers the power for the basic-filed magnet 4 (e.g., about 3 V and about 500 A). The basic-filed magnet 4 is a superconducting magnet with a persistent switch 4a. During a ramp-down, the persistent switch 4a is opened (e.g., by heating), and the current flowing in the magnet is transformed into heat by the protection diode(s) 26. The current delivered to the basic-filed magnet 4 during ramp-up and the current flowing from the basic-filed magnet 4 during ramp-down may be measured by the measuring element 20 including a shunt 20b and a voltmeter 20a that may measure the voltage over the shunt 20b. The current may be determined from the measured voltage and the known resistance of the shunt 20b by using Ohm's law, where the shunt 20b is subject to aging.

Although the present invention has been disclosed in the form of exemplary embodiments and variations thereon, hat numerous additional modifications and variations may be made thereto without departing from the scope of the invention. For the sake of clarity, the use of "a" or "an" throughout this application does not exclude a plurality, and "comprising" does not exclude other steps or elements. The mention of a "unit" or a "device" does not preclude the use of more than one unit or device.

The elements and features recited in the appended claims may be combined in different ways to produce new claims that likewise fall within the scope of the present invention. Thus, whereas the dependent claims appended below depend from only a single independent or dependent claim, it is to be understood that these dependent claims may, alternatively, be made to depend in the alternative from any preceding or following claim, whether independent or dependent. Such new combinations are to be understood as forming a part of the present specification.

While the present invention has been described above by reference to various embodiments, it should be understood that many changes and modifications can be made to the described embodiments. It is therefore intended that the foregoing description be regarded as illustrative rather than limiting, and that it be understood that all equivalents and/or combinations of embodiments are intended to be included in this description.

The invention claimed is:

1. A calibration method for calibrating a measuring element for determining an electric current flowing through a basic-field magnet of a magnetic resonance imaging system, the calibration method comprising:
performing a measurement with the measuring element;
performing a frequency measurement in a magnetic field of the basic-field magnet with a frequency measuring unit, wherein the measurement with the measuring element and the frequency measurement correspond to the same magnetic field of the basic-field magnet;
calculating a calibration factor based on a deviation between the measurement with the measuring element and the frequency measurement; and
calibrating the measuring element or the electric current in the basic-field magnet based on the calibration factor.

2. The calibration method of claim 1, wherein calibrating the measuring element comprises:
calculating corresponding parameters from the measurement with the measuring element and the frequency measurement; and
determining the calibration factor as an aging factor of the measuring element based on a difference of the corresponding parameters.

3. The calibration method of claim 2, wherein calculating the corresponding parameters comprises calculating a magnetic field, an electric current, or a frequency from the measurement with the measuring element and the frequency measurement.

4. The calibration method of claim 2, wherein a phantom or a patient scan is used for the frequency measurement.

5. The calibration method of claim 1, wherein the measurement with the measuring element is performed at a beginning of a ramping procedure, and the frequency measurement is performed before the ramping procedure.

6. The calibration method of claim 5, wherein the basic-field magnet is a superconducting magnet with a persistent switch, and the ramping procedure is performed by opening the persistent switch and determining an electric current flowing through the basic-field magnet by determining a time resolved current-curve based on the measurement with the measuring element.

7. The calibration method of claim 6, wherein the electric current flowing through the basic-field magnet before opening the persistent switch is calculated by reconstructing the current-curve to a point of time of opening the persistent switch.

8. The calibration method of claim 6, wherein determining the electric current flowing through the basic-field magnet comprises measuring a voltage V over a shunt resistance with a predefined or earlier calibrated value R and calculating I with the formula I=U/R.

9. The calibration method of claim 8, wherein the calibration factor scales linear with the deviation of the measured frequency to a predefined target frequency, or
wherein the calibration factor is calculated based on the measured frequency, a constant coefficient, and the determined electric current I from $C=x \cdot I/f$.

10. The calibration method of claim 1, wherein the measurement with the measuring element is performed at an end of a ramping procedure, and the frequency measurement is performed after the ramping procedure.

11. The calibration method of claim 10, wherein the frequency measurement is performed during a patient scan,
wherein the calibration of the measuring element is based on the frequency measurement, and
wherein the calibration is adjusted based on a chronological sequence of succeeding calibration factors measured at different time points or a predefined aging curve.

12. A ramping method for controlling a ramping of a basic-field magnet of a magnetic resonance imaging system, the ramping method comprising:
ramping of a basic-field magnet of a magnetic resonance imaging system,
wherein a magnetic field of the basic-field magnet is ramped from a first magnetic field-strength to a second magnetic field-strength,
wherein an electric current flowing in the basic-field magnet is determined by a measuring element, and
wherein the measuring element is calibrated with a calibration method for calibrating the measuring element for determining the electric current flowing through the basic-field magnet of the magnetic resonance imaging system, the calibration method comprising:
performing a measurement with the measuring element;
performing a frequency measurement in the magnetic field of the basic-field magnet with a frequency measuring unit, wherein the measurement with the measuring element and the frequency measurement correspond to the same magnetic field of the basic-field magnet;
calculating a calibration factor based on a deviation between the measurement with the measuring element and the frequency measurement; and
calibrating the measuring element or the electric current in the basic-field magnet based on the calibration factor.

13. The ramping method of claim 12, wherein the measuring element is calibrated before a ramping procedure with the calibration factor calculated in a preceding ramping procedure.

14. The ramping method of claim 13, wherein the calibration factor is adjusted based on a condition factor from a predefined aging curve or calculated from an extrapolation of a chronological sequence of succeeding calibration factors measured at different time points.

15. The ramping method of claim 13, wherein after the calibration of the measuring element, but before the next ramping procedure, a ramp-adjusting procedure is performed, and
wherein the electric current in the basic field magnet is adjusted based on the calibration of the measuring element.

16. A system for calibrating a measuring element for determining an electric current flowing through a basic-field magnet of a magnetic resonance imaging system, the system comprising:

a first data interface configured to read data from a measurement of the measuring element;

a second data interface configured to read data from a frequency measuring unit, the frequency measuring unit being configured to perform a frequency measurement, wherein the system is configured such that the data of the measurement of the measuring element and the data of the frequency measurement are selected to correspond to the same magnetic field of the basic-field magnet;

a calculation unit configured to calculate a calibration factor based on a deviation between the measurement of the measuring element and the frequency measurement; and a calibration unit configured for calibrating the measuring element based on the calibration factor.

17. A magnet power supply unit for driving a basic-field magnet of a magnetic resonance imaging system, the magnet power supply unit comprising:

a system for calibrating a measuring element for determining an electric current flowing through a basic-field magnet of a magnetic resonance imaging system, the system comprising:

a first data interface configured to read data from a measurement of the measuring element;

a second data interface configured to read data from a frequency measuring unit, the frequency measuring unit being configured to perform a frequency measurement, wherein the system is configured such that the data of the measurement of the measuring element and the data of the frequency measurement are selected to correspond to the same magnetic field of the basic-field magnet;

a calculation unit configured to calculate a calibration factor based on a deviation between the measurement of the measuring element and the frequency measurement; and a calibration unit configured for calibrating the measuring element based on the calibration factor.

18. A control device for controlling a magnetic resonance imaging system, the control device comprising:

a processor configured to calibrate a measuring element for determination of an electric current flowing through a basic-field magnet of a magnetic resonance imaging system, the calibration of the measuring element comprising:

performance of a measurement with the measuring element;

performance of a frequency measurement in a magnetic field of the basic-field magnet with a frequency measuring unit, wherein the measurement with the measuring element and the frequency measurement correspond to the same magnetic field of the basic-field magnet;

calculation of a calibration factor based on a deviation between the measurement with the measuring element and the frequency measurement; and calibration of the measuring element or the electric current in the basic-field magnet based on the calibration factor.

19. A magnetic resonance imaging system comprising:

a magnet power supply unit for driving a basic-field magnet of the magnetic resonance imaging system, the magnet power supply unit comprising:

a system for calibrating a measuring element for determining an electric current flowing through a basic-field magnet of a magnetic resonance imaging system, the system comprising:

a first data interface configured to read data from a measurement of the measuring element;

a second data interface configured to read data from a frequency measuring unit, the frequency measuring unit being configured to perform a frequency measurement, wherein the system is configured such that the data of the measurement of the measuring element and the data of the frequency measurement are selected to correspond to the same magnetic field of the basic-field magnet;

a calculation unit configured to calculate a calibration factor based on a deviation between the measurement of the measuring element and the frequency measurement; and a calibration unit configured for calibrating the measuring element based on the calibration factor.

20. In a non-transitory computer-readable storage medium that stores instructions executable by one or more processors to calibrate a measuring element for determining an electric current flowing through a basic-field magnet of a magnetic resonance imaging system, the instructions comprising:

performing a measurement with the measuring element;

performing a frequency measurement in a magnetic field of the basic-field magnet with a frequency measuring unit, wherein the measurement with the measuring element and the frequency measurement correspond to the same magnetic field of the basic-field magnet;

calculating a calibration factor based on a deviation between the measurement with the measuring element and the frequency measurement; and calibrating the measuring element or the electric current in the basic-field magnet based on the calibration factor.

* * * * *